United States Patent [19]

Dadson et al.

[11] Patent Number: 5,053,003
[45] Date of Patent: Oct. 1, 1991

[54] METHOD AND APPARATUS FOR PERITONEAL DIALYSIS USING A "Y" TUBING SET

[76] Inventors: Joseph E. Dadson, 7 Harrow Smith Place, Richmond Hill, Ontario, Canada, L4E 2E1; Mahesh Agarwal, 7 Grant's Place, Markham, Ontario, Canada, L3S 2W2

[21] Appl. No.: 339,977

[22] Filed: Apr. 18, 1989

[51] Int. Cl.⁵ .............................................. A61M 1/00
[52] U.S. Cl. ...................................... 604/28; 604/29; 604/283; 604/284; 604/411
[58] Field of Search ................ 604/27, 29, 88, 261, 604/263, 283, 284, 411, 256, 905

[56] References Cited

U.S. PATENT DOCUMENTS

| 4,080,965 | 3/1978 | Phillips | 604/411 |
|---|---|---|---|
| 4,346,703 | 8/1982 | Dennehey et al. | 604/29 |
| 4,432,764 | 2/1984 | Lopez | 604/283 |
| 4,445,896 | 5/1984 | Gianturco | 604/238 |
| 4,585,436 | 4/1986 | Davis et al. | 604/29 |
| 4,589,879 | 5/1986 | Pearson | 604/411 |
| 4,624,664 | 11/1986 | Deluso et al. | 604/256 |
| 4,642,091 | 2/1987 | Richmond | 604/29 |
| 4,676,775 | 6/1987 | Zolnierczyk et al. | 604/28 |
| 4,778,447 | 10/1988 | Velde et al. | 604/29 |
| 4,786,286 | 11/1988 | Cerny et al. | 604/406 |
| 4,810,241 | 3/1989 | Rogers | 604/28 |

OTHER PUBLICATIONS

Lopez, Georges, French patent application 2539034, filed 01/01/83, published 13.07.84.
Chernack, Milton P., UK patent application 2111029, filed 02.06.82, published 29.06.83.

Primary Examiner—John D. Yasko
Assistant Examiner—Adam J. Cermak
Attorney, Agent, or Firm—Shoemaker and Mattare, Ltd.

[57] ABSTRACT

An apparatus for carrying out peritoneal dialysis on a patient having a catheter ending in a patient connector, includes a tubing set in a "Y" configuration, including a first, second and third arm. Each arm has a clamp and terminates in a connector. Along with the "Y" tubing set are also provided a cover for covering and protecting the patient connector after the tubing set has been disconnected, and a closure for sealing a dialysate container after it has been emptied, so that it can be used in a subsequent procedure as a drain bag.

4 Claims, 5 Drawing Sheets

METHOD AND APPARATUS FOR PERITONEAL DIALYSIS USING A "Y" TUBING SET

This invention relates to a new "Y" tubing set for use in peritoneal dialysis treatment. Its major purposes are to reduce infection rate, to simplify operational procedure and to provide physical well-being to patients maintained on peritoneal dialysis.

BACKGROUND OF THIS INVENTION

The peritoneal dialysis (PD) modality was introduced before Hemodialysis. However, because of the high infection rates associated with PD treatment, Hemodialysis has become the major modality used for life support of End-Stage-Renal-Failure. This is true for both chronic and acute patients.

Hemodialysis is a direct treatment of blood using an extracorporeal system with an artificial membrane (kidney). PD uses the principles of osmosis and diffusion across the peritoneal membrane to indirectly remove toxic waste and substances from the blood, thereby correcting certain electrolyte and fluid imbalances. By the nature of the operation, PD is a slower but more gentle dialysis technique. The extracorporeal hemodialysis is used more often when rapid and efficient dialysis is necessary because of excessive patient load and/or severe renal failure or drug intoxication.

Technically, hemodialysis is more demanding and restrictive for patients than PD. These along with other medical, economical and social reasons have resulted in steadily increasing use of the simpler PD.

As more attention is paid to PD, new technical improvements are also introduced. The current advances in PD have led to an increasing number of patients using PD at home. Some of these advances have introduced different PD techniques and others have helped to reduce the peritonitis (infection) rate. Peritonitis is by far the most serious complication limiting the growth of PD.

The automated PD techniques such as Intermittent Peritoneal Dialysis (IPD), and Continuous Cyclic Peritoneal Dialysis (CCPD) have proven to reduce the risk of peritonitis. However, since Continuous Ambulatory Peritoneal Dialysis (CAPD) is a simpler form of home PD treatment, the majority of PD patients are trained in this therapy.

With CAPD the patient manually performs four to six fluid exchanges per day using sterile packaged dialysate. Between exchanges the patient carries the dialysate the peritoneal cavity for four or more hours. Of all the PD techniques CAPD has the highest peritonitis rate. Repeated peritonitis may cause scarring of the peritoneal membrane and may reduce membrane permeability and hence dialysis efficiency. These may also lead to premature termination of PD therapy for the patient. Hence the severity and frequency of peritonitis have led to many technical advances and techniques all directed for use with CAPD.

The "povidone-iodine clamp" is supposed to prevent bacterial penetration through the catheter lumen. The "UV-XD Ultraviolet Germicidal System" is supposed to reduce bacterial counts during the bag exchange. The "Sterile Connection Device" provides sterile "heat-weld" between the patient line and dialysate solution bag. The "Peridex CAPD Filter Set" is meant to prevent bacteria from entering the peritoneal cavity.

Unfortunately, none of these special devices has proven capable of significantly reducing the peritonitis rate in any controlled studies, and the search has continued for a device or technique which will remove this impediment from the PD population.

The recent application of the "Y" tubing set has exhibited a major promise of peritonitis rate reduction in CAPD. However, the complexities and unrefined procedure of the "Y" set have not made "Y" set operation friendly to the patients. Hence, poor patient compliance, which leads to poor aseptic technique, has masked any great beneficial contribution of the "Y" set to reduction of the peritonitis rate.

Two recent developments of the "Y" set will be described subsequently in this disclosure, along with their shortcomings. This description will be made with reference to the drawings.

GENERAL DESCRIPTION OF THIS INVENTION

In view of the drawbacks of conventional approaches to PD at the present time, as described both previously and subsequently, it is an aim of one aspect of this invention to provide an apparatus and a method for carrying out continuous ambulatory peritoneal dialysis (CAPO) in such a way that the patient does not need to carry the "Y" tubing set on his person between treatments, and such that temporary disconnection from the "Y" tubing set during the PD phase can be accomplished without significant risk of infection. More particularly, this invention provides a method for carrying out peritoneal dialysis on a patient whose peritoneal cavity is in fluid communication, via a tubular pathway, with a threaded patient connector, utilizing an apparatus comprising:

a tubing set having first, second and third tubing arms, each tubing arm having a first end and a second end, the first end of each tubing arm being connected to and in communication with the first ends of the other two arms, first connecting means on the second end of the first tubing arm, said first connecting means being threaded and adapted to be connected to said threaded patient connector, second connecting means on the second end of the second tubing arm, said second connecting means being adapted to be connected to a fresh dialysate container, third connecting means on the second end of the third tubing arm, said third connecting means being adapted to be connected to a drain bag, clamping means at an intermediate location of each tubing arm, threaded cover means for engaging, covering and protecting the patient connector after the tubing set has been used and disconnected, said threaded cover means being initially closed by a threaded cap, both the cover means and its cap being filled with disinfectant, closure means for sealing a dialysate container after it has been emptied, said method comprising the steps:
a) closing all said clamping means,
then in any order:
threaded connecting the first connecting means to the patient connector, connecting the second connecting means to a fresh dialysate container, and connecting the third connecting means to a drain bag,
then in consecutive order:

c) opening the clamping means on the second and third tubing arms, d) allowing sufficient time for dialysate from said container to flow through the second and third tubing arms and into the drain bag, thus flushing the second and third tubing arms, e) closing the clamping means on the second tubing arm, f) opening the clamping means on the first tubing arm, g) allowing dialysate in the patient's peritoneal cavity to drain into the drain bag, h) closing the clamping means on said third tubing arm, i) opening the clamping means on the second tubing arm and allowing dialysate to flow from the container into the patient's peritoneal cavity, j) closing the clamping means on the second tubing k) closing the remaining clamping means, l) disconnecting the patient connector from said first connecting means by unscrewing, m) removing the cap from the cover means by unscrewing, then in any order:

n) threadably connecting the cover means to the patient connector, and o) threadably connecting the cap to said first connecting means.

GENERAL DESCRIPTION OF THE DRAWINGS

Two embodiments of this invention are illustrated in the accompanying drawings, in which like numerals denote like parts throughout the several view, and in which.

DETAILED DESCRIPTION OF THE DRAWINGS

Figure 5:
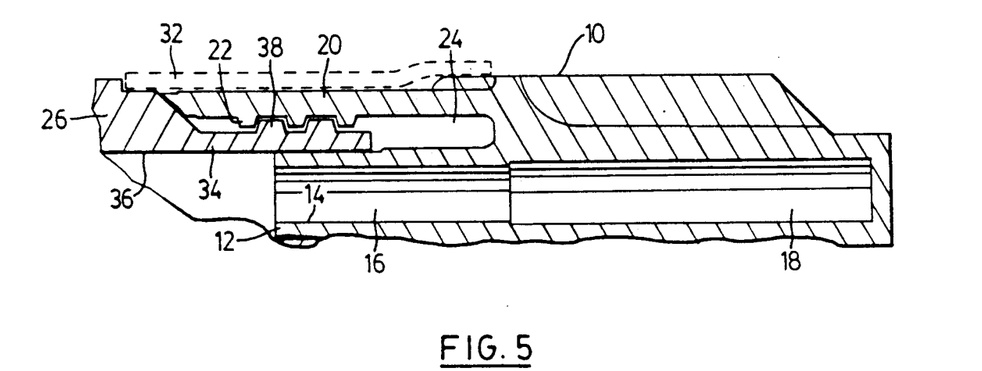
FIG. 5 is a partial axial sectional view of the item shown in FIG. 7.

Attention is first directed to FIG. 5 which show an integral cover 10 which includes a substantially cylindrical central probe 12 with a leading end 14. The probe 12 is hollow, as can be seen at 16 in FIG. 5, the hollow interior of the probe 12 communicating with a recessed chamber 18. It will be seen that the chamber 18, including the hollow interior 16 of the probe 12, is blind at the rightward end in FIG. 5, and opens only through the leading end 14 of the probe 12. The cover 10 further includes a cylindrical portion 20 which is substantially coaxial with the probe, and has an internal thread 22, the purpose of which will become clear in what follows.

The cover 10 further defines an additional chamber 24 of annular configuration lying outside of the probe 12 and inside the cylindrical portion 20.

Figures 7, 8:
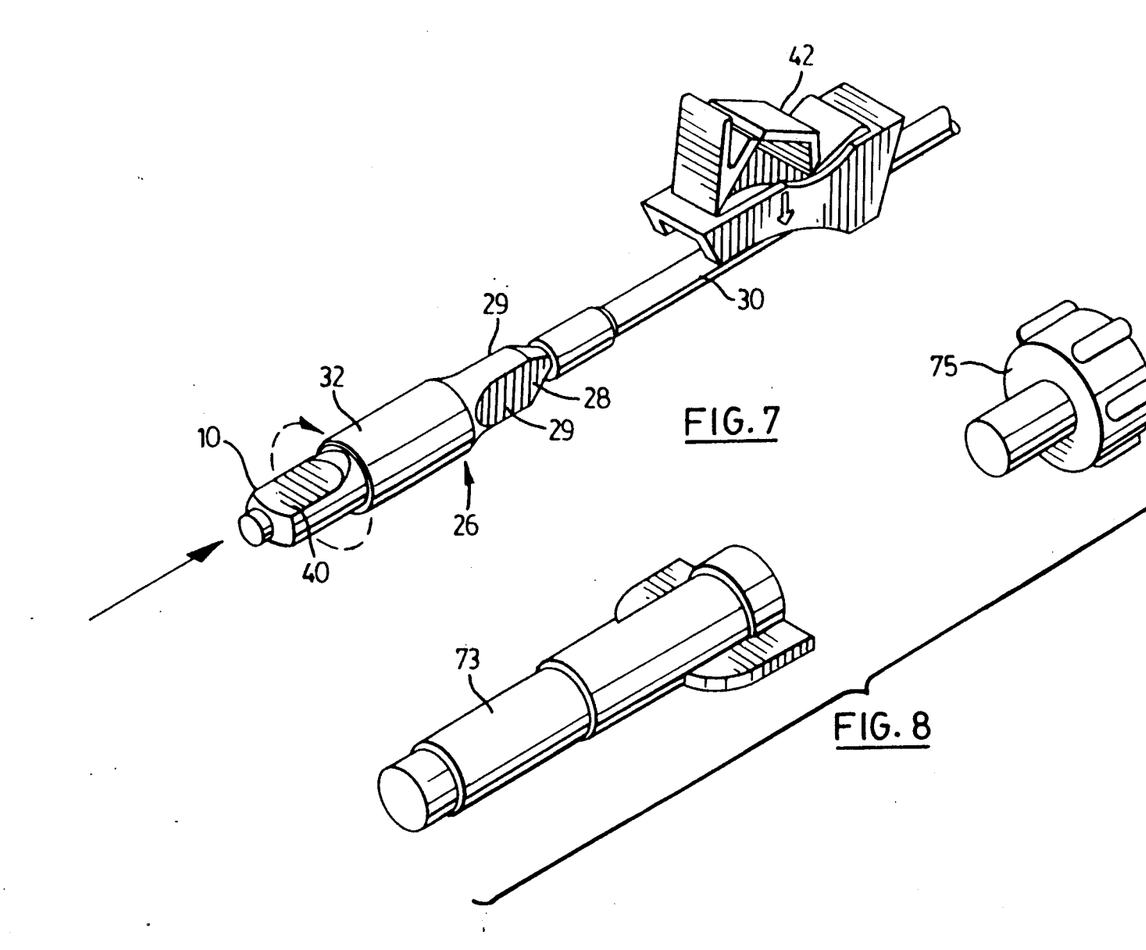
FIG. 7 is a perspective view of one end of a patient transfer set.
FIG. 8 is an exploded perspective view of a cartridge for use in a variant of this invention.

The cover which is illustrated at 10 in FIG. 5 is adapted to close a connector shown at 26 in FIG. 7, and shown partly in section in FIG. 5.

Looking at FIG. 7, the connector 26 has a rearward portion 28 exhibiting two flats at 29 for ease of handling, and having a standard tubular portion adapted to connect to a flexible tubing 30 which may be either the patient's catheter or the tube of a transfer set which in turn is connected to the patient's catheter. In FIG. 7, the leftward end of the connector 26 is covered by a resilient sleeve member 32 which is shown in broken lines in FIG. 5. The sleeve member 32 covers and protects a neck portion 34 (see FIG. 5) having an external thread 38, and an opening central passageway 36 in fluid communication with said standard tubular portion. As can be seen in FIG. 5, the external thread 38 engages the internal thread 32, and at the same time the leading end 14 of the probe 12 enters the passageway 36. The probe 12 is sized to be snugly received in the passageway 36.

The Figures show that the remainder of the cover 10 (the portion to the right in FIG. 5) is shaped to define two flats 40, on opposite sides, to facilitate manipulation.

In FIG. 7, a conventional clamp is shown at 42.

FIG. 7 can also be taken to represent the condition of a typical transfer set, as packaged. In accordance with one aspect of this invention, the packaged transfer set (ready to be connected to the patient's catheter and then to the tubing set) would include a cover 10 exactly as described above. When the connector 26 (FIG. 7) is ready to be connected to the tubing set, the cover 10 shown in FIG. 7 (i.e. the original cover closing the connector 26 of a transfer set in the packaged condition) is removed by rotating counterclockwise and then is discarded.

The connector 26 shown in FIG. 7 is then ready to be connected to the tubing set leading to one or more dialysate bags and one or more drain bags or the equivalent.

THE PRIOR ART

Earlier in this specification mention was made of recent developments involving "Y" tubing sets. In actual fact, "Y" tubing sets have been used for manual PD treatment for many years before CAPD was developed. The major difference is that the CAPD "Y" set is much simplified, with no sampling port or drip chambers.

Figure 1:
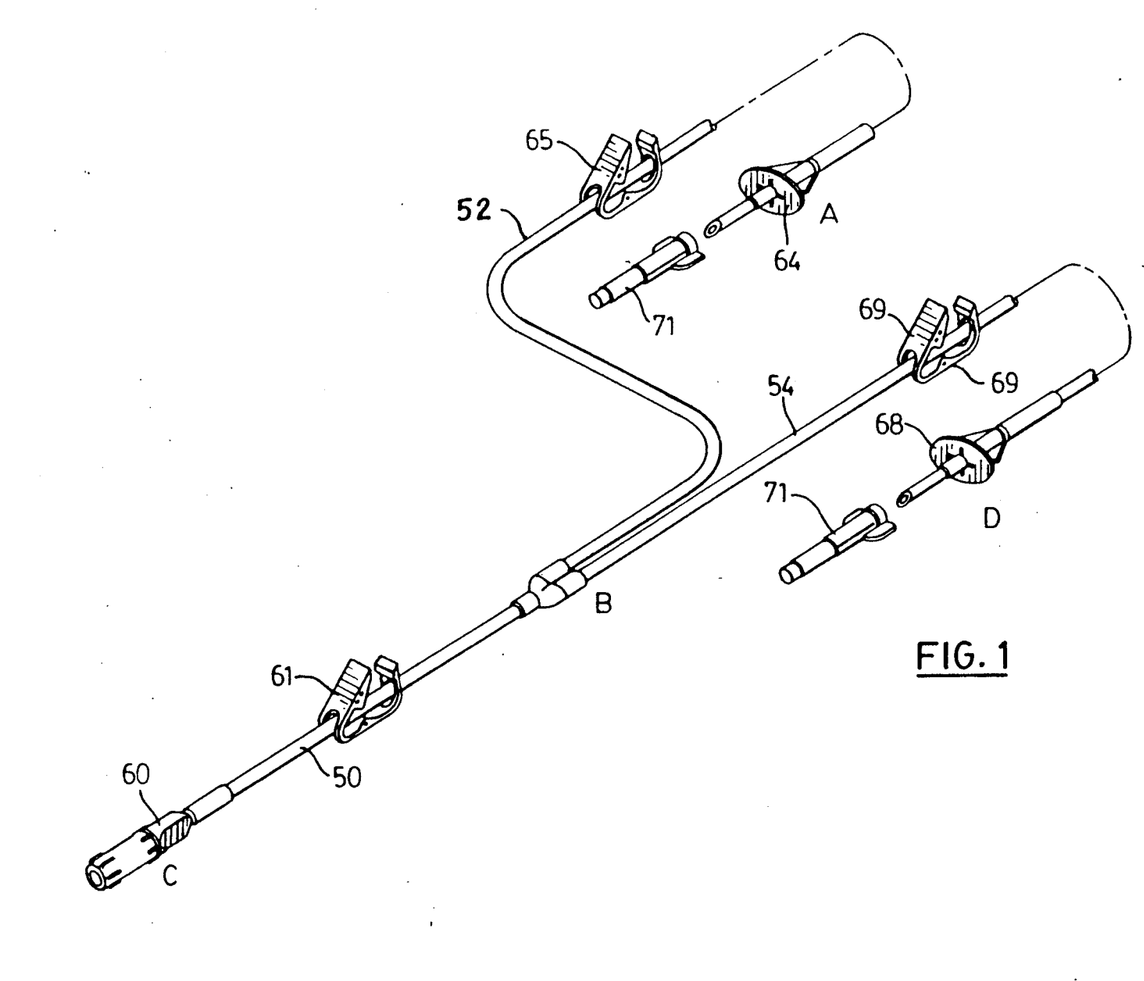
FIG. 1 is perspective view of a first embodiment of this invention, and is also useful for an understanding of the prior art.

The conventional "Y" set is represented in FIG. 1. It is composed of a stem CB, and two arms AB and BD. The stem CB is identified by the numeral 50, and the arms AB and BD are represented by the numerals 52 and 54, respectively. The arm AB (52), intended for connection to the dialysis solution container, is normally longer than the drain arm BD (54). The stem CB (50) is connected to the patient connector, shown at 26 in FIG. 7. It should be noted that the connector 26 can be placed at the end of the catheter itself, or more commonly constitutes one end of a transfer set, which is a short tubular item which is in turn connected to the patient's catheter. In the remainder of this disclosure and the appended claims, the item 26 shown in FIG. 7 will be referred to as the patient connector, whether that connector is on a transfer set or directly on the patient catheter.

Generally, the "Y" set described above is replaced once a month because of the danger of infection arising if the "Y" is removed. As a result, the CAPD patients have to wear the "Y" set between dialysis fluid exchanges. In order to maintain the integrity of the "Y" set, the arms AB and BD of the set, when not being used, are filled with disinfectant and then capped off.

To perform fluid exchange, the arm AB is connected to a new dialysate container. The of arm BD is suspended over a drain container. These two arms are then unclamped. A small amount of the fresh dialysate is used to rinse out the disinfectant from the arms AB and BD, whereupon the arm AB is again clamped. The tube CB is unclamped and the patient drains out the spent dialysate from the peritoneal cavity into the drain container along CB and BD.

At the end of the drain, the line BD is closed and line AB is opened again. The rest of the fresh dialysate is passed into the patient. When the dialysate container is emptied, the stem CB is clamped and the arm AB is removed from the empty container. Then, the two arms AB and BD are completely filled with disinfectant and capped off. The patient rolls up the whole "Y" set, stores it in a special bag and carries it on the body until the next exchange.

The main shortcomings of the above-described current "Y" set procedure are:
  (i) The bulkiness of the tubing set that the patients have to carry with them at all times.
  (ii) The risk of accidental infusion of disinfectant into the peritoneum cavity. This is known to cause "chemical" peritonitis which may cause scarring of the peritoneal membrane. Above all it is a painful incident, especially if the disinfectant used is Amuchina.
  (iii) The operation is long, complicated and requires many containers and bottles. Hence the exchange procedure is preferably carried on at one set location each time.

Some attempts have been made to reduce the above-mentioned deficiencies of the "Y" set. The second-generation "Y" sets are meant to be non-wearables. They are generally in the same form as shown in FIG. 1, but they include a drain bag attached to the drain arm DB.

During operation of the second-generation "Y" set, the spent dialysate is collected in the drain bag. When the fresh dialysate is completely emptied into the patient, the "Y" set is discarded. A special connector cover is used to cap off the patient connector.

Because the second-generation "Y" set comes with a drain bag, the cost of this set is unfortunately high. Since the procedure is done four to six times a day, seven days a week, the annual operational cost per patient is very high indeed.

THE PRESENT INVENTION

The present "Y" set invention eliminates the shortcomings of all the other "Y" sets so far introduced into the PD modality. Above all, this "Y" set could be used for both manual PD and CAPD treatments.

Figure 2:
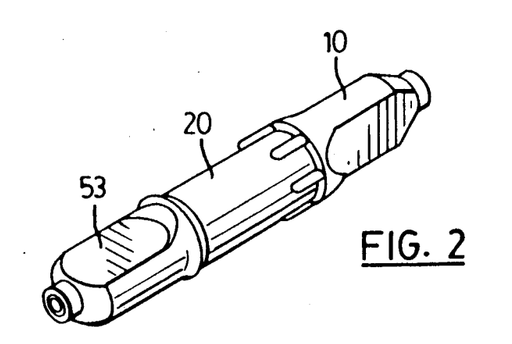
FIG. 2 is a perspective view of a cover means and its associated cap for use in association with the "Y" tubing set forming part of this invention.
Figure 3:
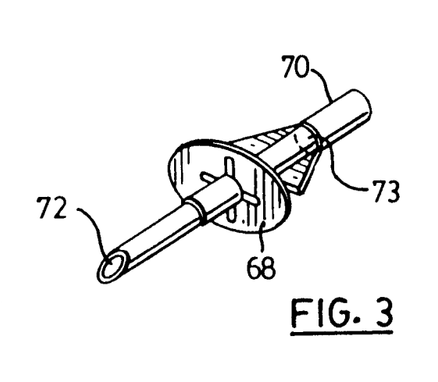
FIG. 3 is a blind spike useful in carrying out one form of this invention.

One form of this invention is constituted by a package which contains the "Y" set shown in FIG. 1, the item shown in FIG. 2, and optionally the item shown in FIG. 3. All of these are supplied in sterile condition in a single PD package.

The connector 60 mates with the patient's catheter connector or transfer set connector. If a transfer set is used, the transfer set is attached to the patient's PD catheter and the transfer set is changed either once a month or once every six months or more. The connector to which the connector 60 is attached is referred to in the claims as the "patient connector". The connectors and clamps are preferably colour coded for easy identification. The patient connector 60 and clamp 61 may be white, the fill connector 64 and clamp 65 may be colored red, and the drain connector 68 and clamp 69 may be blue. The connectors 64 and 68 are identical and have the conventional "spike" shape. They are protected by conventional covers 71, which are removed prior to a treatment. The fill line is connected to a fresh dialysate container by means of the red connector A. The drain line is connected to an empty drainage bag by means of the blue connector 68. The empty drainage bag is obtained by utilizing the empty fresh dialysate bag at the end of the previous fluid exchange.

The type of "Y" set connectors and accessories required will depend on the type of fresh dialysate containers in use. The "Y" set used for fresh dialysate bags which accept spikes, has connectors 64 and 68 as red and blue spikes respectively (using the color key suggested above). The set is also packaged with connector cover 10 and cap 53 (prefilled with disinfectant), and optionally a blue closed spike 70 seen in FIG. 3. The spike 70 is identical externally to the connectors 64 and 68, the only difference being that the internal passageway 72 is closed by an internal partition 73.

During dialysate exchange the patient closes all clamps and connects the "Y" set to the patient connector. The red connector 64 is connected to a fresh dialysate bag. A closed blue spike like that in FIG. 3 is removed from the empty dialysate bag saved from the previous exchange. The blue connector 68 of the "Y" is inserted into the empty dialysate bag. This bag now becomes the empty drain bag.

To perform Flush-Before-Fill, which is very important, the white clamp 61 remains closed while the red fill clamp 65 and the blue drain clamp 68 are opened for approximately five seconds. This causes the lines AB and BD to be flushed with fresh dialysate. Next, the red clamp 65 on fill line AB is closed and the white clamp 61 on the patient line CB is opened. The spent dialysate drains out from the patient into the drain bag along CB and BD. At the end of the drain phase, the blue clamp 69 on the drain line BD is closed. The line AB (red clamp 65) is opened again to allow fresh dialysate to fill the patient.

When the dialysate bag is empty, all the line clamps 61, 65 and 69 are closed. The "Y" set is then disconnected from the transfer set (the patient connector). The main body of the connector cover 10 is used to cap-off and protect the patient connector (e.g. the connector leading to the patient's catheter). The red fill spike 64 is removed from the empty dialysate bag. In its place, the sterile closed blue spike 70 is inserted into the empty bag and safely kept for the next fluid exchange. This bag will serve as the empty drainage bag for the next exchange.

The "Y" set used for Luer Lock dialysate solution bags (such as Travenol (trade mark) System II bags), comes with red and blue female Luer connectors 64a and 68a respectively. See FIG. 4. This "Y" set version is packaged with only the connector cover 10. The blue closed spike 70 is not included because it is not used here.

Figure 4:
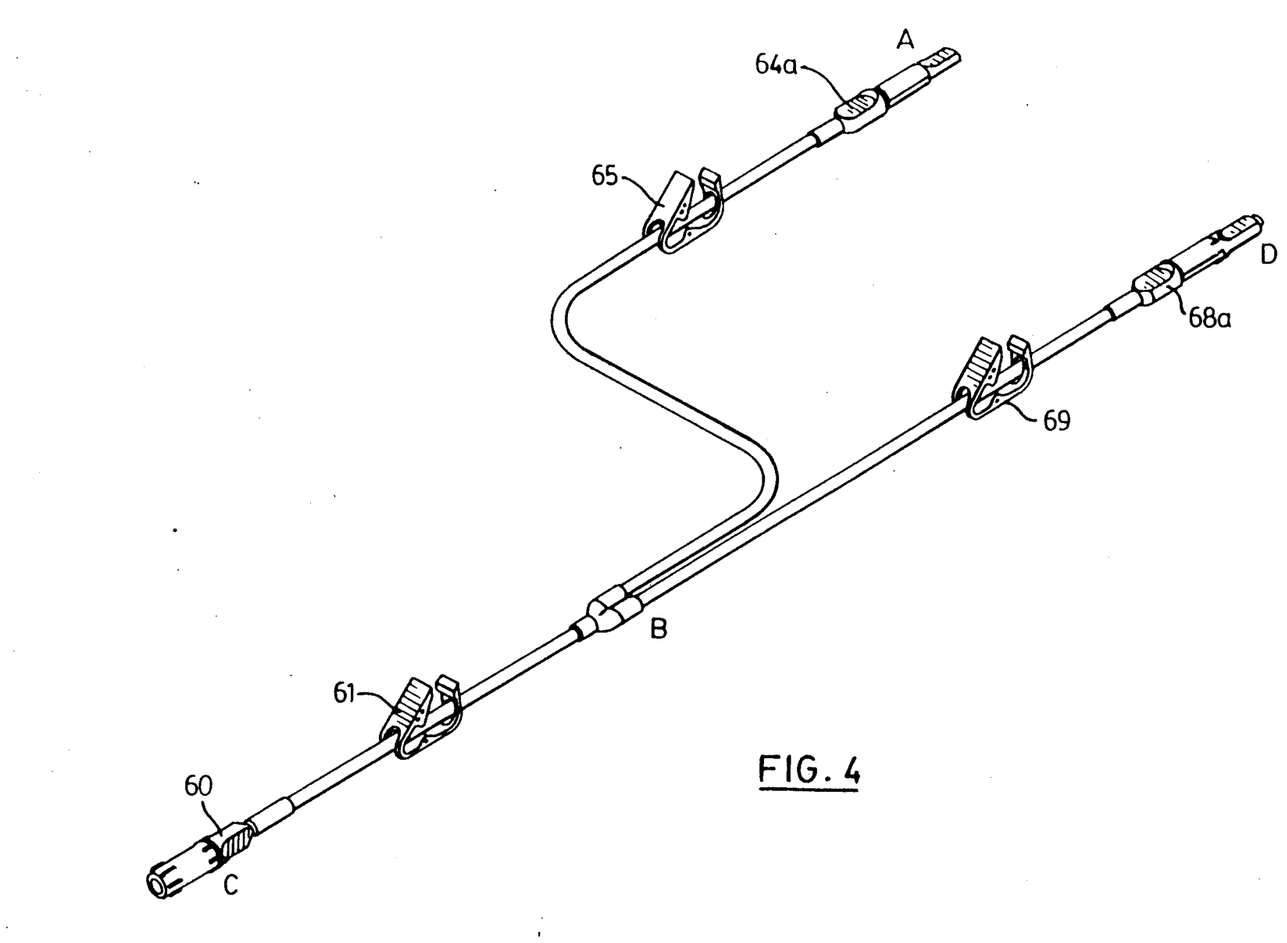
FIG. 4 is a perspective view of a different "Y" tubing set forming the second embodiment of this invention.

During fluid exchange the "Y" tubing set of FIG. 4 is connected in the same manner as described above with respect to FIG. 1. The only difference is the disconnection procedure from the transfer set, allowing the patient to be free of the apparatus during the dialysis phase, when the dialysate is inside the peritoneal cavity. The first step in disconnection is to remove the "Y" set from the transfer set (patient connector). The male body of the connector cover 10 is used to cover and protect the patient (transfer set) connector. The empty dialysate bag is disconnected from the red fill connector 64a. Then the blue female cap 53 of the cover 10 is used to close the empty dialysate bag. This closed empty bag is saved to be used as a drainage bag during the next fluid exchange.

A second version of this invention is such that the "Y" set has multiple "arms" AB (52) with a corresponding number of fill connectors 64 or 64a. These multiple arms make it possible to connect the "Y" set to many dialysis solution containers at the same time. The second version of the "Y" set could be used in many ways for peritoneal dialysis treatment. However the two major applications are:
 (a) for setting up a CAPD system for a patient unable to perform his/her own solution container connection (i.e. very old patients, blind patients and children) and
 (b) for initiating peritonitis treatment protocols.

When using this second version for regular peritoneal dialysis a multiple of fresh dialysate containers would be set up only once under controlled aseptic conditions. The patient then connects his catheter or transfer set (the patient connector) to the "Y" set for fluid exchange. For each fluid exchange, only one fresh dialysate container is used. The other fresh dialysate containers remain closed up. After each fill the patient disconnects completely from the system using the connector cover 10 to cap-off, protect and disinfect the patient connector. The cap 53 of cover 10 is used to cap-off, protect and disinfect the "Y" set connector 60.

To reconnect the patient back to the system, the cover 10 is removed from the patient connector, the cap is removed from connector 60 of the "Y" set, and immediately the patient connector is reconnected to connector 60.

When using the second version for peritonitis treatment protocol, a number of fresh dialysate containers are set up at the same time. The antibiotic doses are added to the required number of dialysate containers. The containers of fresh dialysate without antibiotic are first used to quickly flush the peritoneum cavity. Then the dialysate containers with antibiotic are used one by one to provide treatment to the patient.

This "Y" set invention therefore is functionally superior to the other "Y" sets currently in use.
 (i) The patients do not have to wear the bulky set between dialysate exchange; it is a non-wearable set.
 (ii) No disinfectant of the "Y" arms is necessary, which therefore
  (a) eliminates accidental infusion of disinfectant into patients,
  (b) eliminates accidental bleaching of patient's clothing
  (c) shortens fluid exchange time, and
  (d) requires no bulky disinfectant containers or disinfectant applicators to be carried around.
 (iii) The cover 10 (supplied prefilled with disinfectant) enables easy and quick cap-off of the patient connector.
 (iv) The two parts of the connector 10 are functionally useful, thus reducing cost.
 (v) The saving of the empty dialysate bag (or container) to be used as the next drainage bag reduces the cost of the system.
 (vi) Color-coded connectors and clamps provide easy identification of lines, ensure a short training period and eliminate operational errors.
 (vii) The absence of a fixed bag on the drain line facilitates
  (a) the collection of an effluent sample for testing;
  (b) the draining of excess fluid from the patient;
  (c) open draining into any receptacle if so desired by patients, and
  (d) the reduction of costs.

Figure 6:
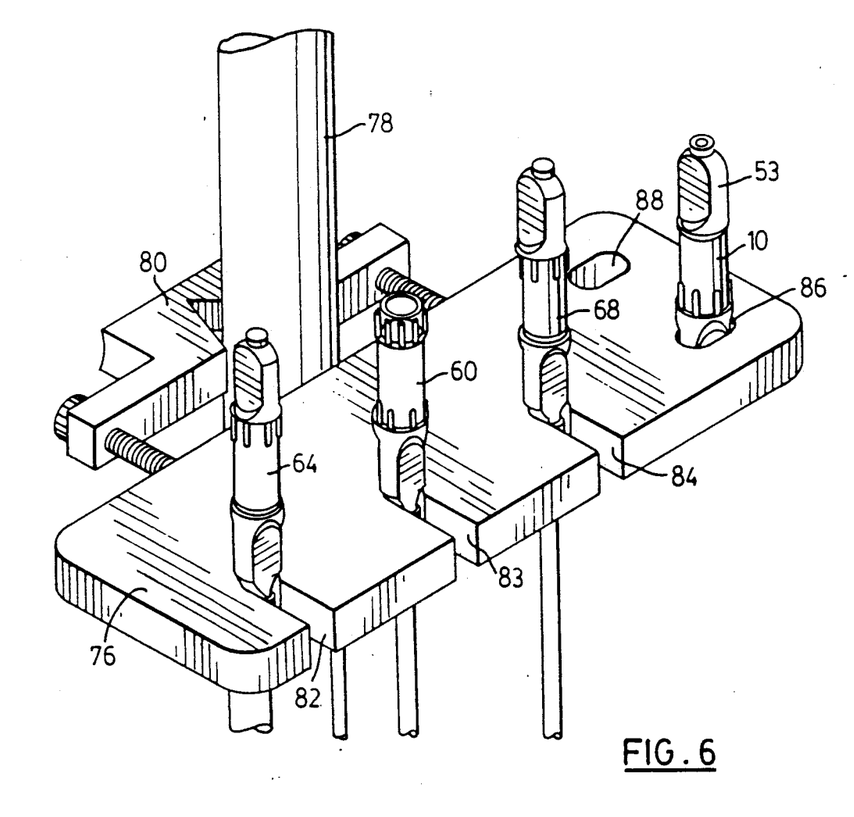
FIG. 6 is a perspective view of an optional tray which can be used to facilitate the method of this invention.

A special "Y" set organizer 76 is also provided (FIG. 6). During fluid exchanges the "Y" set and accessories are arranged in an orderly fashion on the organizer 76. It simplifies material handling and ensures systematic operation of the procedure.

Looking at FIG. 6, the organizer 76 is in the form of a horizontal plate which can be clamped to an upright pole 78 by means of a clamp 80. The organizer 76 provides 3 slots 82, 83 and 84, along with two recesses 86 and 88. The connectors 64, 60 and 68 are shown to be received in the slots 82, 83 and 84, respectively, while the cover 10 and its associated cap 53 is received in the recess 86. The other recess 88 allows storage of cap 53 when removed from the cover 10.

It will be useful here to recapitulate the various process steps involving hook-up, drainage of previous dialysate from the patient, and filling the patient with new dialysate.

The first operation is to connect the "Y" tubing set to the new dialysate bag, to the drainage bag, and to the patient connector (typically a connector on the end of the patient's transfer set). For this operation the organizer 76 shown in FIG. 6 is useful.

Before connecting these various connectors, all of the clamps 61, 65 and 69 are closed. Then, in any order, the following is done: 1) the connector 60 is connected to the patient connector; 2) the connector 64 is connected to a fresh dialysate container or bag; and 3) the connector 68 is connected to a drain bag.

The clamps 65 and 69 on the arms 52 and 54 are then opened, so that dialysate from the container of fresh dialysate can flow through the second and third tubing arms 52 and 54 and into the drain bag. This procedure takes about five seconds, and accomplishes the flushing out of the second tubing arms 52 and 54.

The clamp 65 on arm 52 is then closed, and the clamp 61 on the first tubing arm 50 is opened. Any clamp on the patient's catheter or transfer set should also be opened at this point. Since the tubing arm 50 and 54 are now open, dialysate in the patient's peritoneal cavity can drain into the drain bag. Once this has been accomplished, the clamp 69 on the tubing arm 54 is closed.

By now opening the clamp 65 on the tubing arm 52, dialysate can flow from the container of fresh dialysate into the patient's peritoneal cavity. After this step has been completed, all remaining clamps are closed.

In the event that the patient needs to temporarily disconnect from the tubing set (and reconnect to it at a later time), the procedure is as follows:
 1) the patient connector is disconnected from the connector 60 after all clamps have been closed;
 2) the cap 53 is then removed from the cover 10 and, in any order:

3) the cover 10 is connected to the patient connector, and 4) the cap 53 is connected to the connector 60.

The patient can then go to some other part of the hospital for tests, etc., use the washroom, or whatever, and then return to the dialysis apparatus and reconnect the patient connector to the connector 60. Because both of these joined elements have been in contact with disinfectant, the risk of infecting the patient's peritoneal cavity is virtually non-existent.

In FIG. 8 is illustrated a cartridge 73 and a cap 75 therefor. The cartridge 73 is sized to snugly receive the end of the spike 64, and is useful in the event that the user wishes to re-use a "Y" tubing set for several dialysis treatments (rather than being thrown away after a single treatment). The cartridge is capped and filled with liquid disinfectant, when initially provided. At the end of a treatment, the spike 64 is removed from the dialysate bag and is inserted into a cartridge 73. This will maintain the spike 64 in an antiseptic condition between sequential uses of the "Y" tubing set. To re-use the tubing set, the cartridge 73 is removed and the spike 64 is inserted into the next dialysate bag.

While several embodiments of this invention have been illustrated in the accompanying drawings and described hereinabove, it will be evident to those skilled in the art that changes and modifications may be made therein without department from the essence of this invention, as set forth in the appended claims.

The embodiments of the invention in which an exclusive property or privilege is claimed are defined as follows:

1. A method for carrying out peritoneal dialysis on a patient whose peritoneal cavity is in fluid communication, via a tubular pathway, with a threaded patient connector, utilizing an apparatus comprising:
   a tubing set having first, second and third tubing arms, each tubing am having a first end and a second end, the first end of each tubing arm being connected to and in communication with the first ends of the other two arms,
   first connecting means on the second end of the first tubing arm, said first connecting means being threaded and adapted to be connected to said threaded patient connector,
      second connecting means on the second end of the second tubing arm, said second connecting means being adapted to be connected to a fresh dialysate container,
   third connecting means on the second end of the third tubing arm, said third connecting means being adapted to be connected to a drain bag,
   clamping means at an intermediate location of each tubing arm,
   threaded cover means for engaging, covering and protecting the patient connector after the tubing set has been used and disconnected, said threaded cover means being initially closed by a threaded cap, both the cover means and its cap being filled with disinfectant,
   closure means for sealing a dialysate container after it has been emptied,
   said method comprising the steps:
      a) closing all said clamping means,
      b) then in any order: threadably connecting the first connecting means to the patient connector, connecting the second connecting means to a fresh dialysate container, and connecting the third connecting means to a drain bag,
   then in consecutive order:
      c) opening the clamping means on the second and third tubing arms,
      d) allowing sufficient time for dialysate from said container to flow through the second and third tubing arms and into the drain bag, thus flushing the second and third tubing arms,
      e) closing the clamping means on the second tubing arm,
      f) opening the clamping means on the first tubing arm,
      g) allowing dialysate in the patient's peritoneal cavity to drain into the drain bag,
      h) closing the clamping means on said third tubing arm,
      i) opening the clamping means on the second tubing arm and allowing dialysate to flow from the container into the patient's peritoneal cavity,
      j) closing the clamping means on the second tubing arm,
      k) closing the remaining clamping means,
      l) disconnecting the patient connector from said first connecting means by unscrewing,
      m) removing the cap from the cover means by unscrewing, then in any order:
      n) thereby connecting the cover means to the patient connector, and
      o) threadably connecting the cap to said first connecting means.

2. The method claimed in claim 1, in which, after all of the dialysate in a given container has been transferred to the patient's peritoneal cavity, said given container is re-used as a drain bag.

3. The method claimed in claim 1, in which the apparatus includes at least one cartridge containing disinfectant, the cartridge being adapted to close and disinfect said second connecting means, whereby the tubing set can be used for more than a single dialysis treatment.

4. An apparatus for carrying out continuous ambulatory peritoneal dialysis on a patient whose peritoneal cavity is in communication, via a tubular pathway, with a threaded patient connector, the apparatus comprising:
   a tubing set having first, second and third tubing arms, each tubing arm having a first end and a second end, the first end of each tubing arm being connected to and in communication with the first ends of the other two arms,
   first connecting means on the second end of the first tubing arm, said first connecting means being threaded and adapted to be connected to said threaded patient connector,
   second connecting means on the second end of the second tubing arm, said second connecting means being adapted to be connected to a fresh dialysate container,
   third connecting means on the second end of the third tubing arm, said third connecting means being adapted to be connected to a drain bag,
   clamping means at an intermediate location of each tubing arm,
   threaded cover means for covering and protecting the patient connector after the tubing set has been used and disconnected, the cover means being closed by a threaded cap, both the cover means and the cap being filled with disinfectant, said cap being adapted to threadably seal said first connecting means after disconnection of the tubing set from the patient connector, while the cover means threadably closes and protects the patient connector, in order to allow the patient to completely disconnect from the tubing set during the peritoneal dialysis phase of the treatment, prior to reconnecting back to the same set to continue with the treatment, closure means for sealing a dialysate container after it has been emptied, and wherein said closure means is a closed spike, said second connecting means being an open spike.

* * * * *